(12) United States Patent
Miller et al.

(10) Patent No.: US 10,486,179 B2
(45) Date of Patent: Nov. 26, 2019

(54) DISPENSERS WITH SENSORS TO DETECT SURFACES AND SURFACE CHARACTERISTICS

(71) Applicant: L'Oreal, Paris (FR)

(72) Inventors: Zane Bowman Allen Miller, Seattle, WA (US); Vincenzo Casasanta, III, Woodinville, WA (US); John Streeter, Redmond, WA (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 15/387,515

(22) Filed: Dec. 21, 2016

(65) Prior Publication Data

US 2018/0169682 A1   Jun. 21, 2018

(51) Int. Cl.
| | | |
|---|---|---|
| *A61M 11/02* | (2006.01) | |
| *B05B 12/08* | (2006.01) | |
| *B05D 1/02* | (2006.01) | |
| *B05B 12/02* | (2006.01) | |
| *B05B 12/12* | (2006.01) | |
| *B05B 17/06* | (2006.01) | |
| *A61M 11/00* | (2006.01) | |
| *A61M 35/00* | (2006.01) | |
| *B05B 17/00* | (2006.01) | |
| *B05B 1/06* | (2006.01) | |
| *B05B 7/24* | (2006.01) | |

(52) U.S. Cl.
CPC ........... *B05B 12/02* (2013.01); *A61M 11/005* (2013.01); *A61M 11/006* (2014.02); *A61M 11/02* (2013.01); *A61M 35/00* (2013.01); *B05B 12/122* (2013.01); *B05B 12/124* (2013.01); *B05B 17/0607* (2013.01); *B05B 17/0646* (2013.01); *B05B 17/0669* (2013.01); *B05D 1/02* (2013.01); *B05B 1/06* (2013.01); *B05B 7/2405* (2013.01); *B05B 12/084* (2013.01); *B05B 17/0623* (2013.01)

(58) Field of Classification Search
CPC ....................................................... B05B 12/02
USPC ....................................................... 427/421.1
See application file for complete search history.

(56) References Cited

U.S. PATENT DOCUMENTS 5,352,297 A    10/1994  Peters
5,452,267 A  *  9/1995  Spevak ................. G10K 13/00
                                                                310/328

(Continued)

FOREIGN PATENT DOCUMENTS

| EP | 2197313 A1 | 6/2010 |
|---|---|---|
| EP | 2457065 A1 | 5/2012 |
| WO | 2016/154512 A1 | 9/2016 |

OTHER PUBLICATIONS

International Search Report and Written Opinion dated Mar. 15, 2018, issued in corresponding International Application No. PCT/US2017/066848, filed Dec. 15, 2017, 17 pages.

*Primary Examiner* — Alexander M Weddle
(74) *Attorney, Agent, or Firm* — Christensen O'Connor Johnson Kindness PLLC (57) ABSTRACT

A sprayer that senses the presence or character of a surface to be sprayed includes one or more sensors configured to detect a presence or character of a surface to be sprayed; and a dispenser assembly including one or more components configured to modify at least one spray characteristic of a formulation based on an input from at least one of the one or more sensors indicative of the presence or character of the surface to be sprayed.

22 Claims, 2 Drawing Sheets

(56) References Cited

U.S. PATENT DOCUMENTS

| | | | |
|---|---|---|---|
| 7,841,335 B2 | 11/2010 | Harrington et al. | |
| 8,382,008 B1* | 2/2013 | Ricciardi | A61L 2/22 |
| | | | 239/102.2 |
| 2005/0103891 A1* | 5/2005 | Abergel | A61L 9/12 |
| | | | 239/333 |
| 2006/0118039 A1 | 6/2006 | Cooper | |
| 2008/0265052 A1 | 10/2008 | Quan et al. | |
| 2009/0157015 A1* | 6/2009 | Lotterhos | B05B 15/12 |
| | | | 604/289 |
| 2010/0291310 A1* | 11/2010 | Hartmann | B25J 15/0019 |
| | | | 427/427.3 |
| 2011/0315786 A1* | 12/2011 | Kambayashi | B05B 17/0646 |
| | | | 239/102.2 |
| 2012/0069178 A1 | 3/2012 | Nielsen et al. | |
| 2013/0296811 A1* | 11/2013 | Bangera | A61M 35/00 |
| | | | 604/290 |
| 2014/0250576 A1* | 9/2014 | Pasquini | A47K 17/00 |
| | | | 4/223 |
| 2014/0339323 A1* | 11/2014 | Bentvelsen | A61M 11/005 |
| | | | 239/11 |
| 2015/0141975 A1 | 5/2015 | Bangera et al. | |
| 2015/0202387 A1* | 7/2015 | Yu | B06B 1/0253 |
| | | | 128/200.16 |
| 2015/0239148 A1* | 8/2015 | Israel | B33Y 10/00 |
| | | | 264/40.3 |

* cited by examiner

DISPENSERS WITH SENSORS TO DETECT SURFACES AND SURFACE CHARACTERISTICS

SUMMARY

In an aspect, a sprayer that senses the presence or character of a surface to be sprayed includes one or more sensors configured to detect a presence or character of a surface to be sprayed, and a dispenser assembly including one or more components configured to modify at least one spray characteristic of a formulation based on an input from at least one of the one or more sensors indicative of the presence or character of the surface to be sprayed.

In an embodiment, the dispenser assembly includes one or more of a jet dispenser, a vibrating mesh dispenser, and an ultrasonic wave dispenser.

In an embodiment, the spray characteristic includes one or more of a spray flow rate, a spray angle, a spray distance, a spray drop density, a spray drop size, a spray drop uniformity, a spray pattern, a spray pattern shape, a spray spaced-apart pattern, a spray stream direction, a spray velocity, and a spray volume based on an input from at least one of the one or more sensors indicative of the presence or character of the surface to be sprayed.

In an embodiment, the dispenser assembly includes one or more components configured to modify at least one spray characteristic of a formulation based on an input from at least one of the one or more sensors indicative of a surface area to be sprayed.

In an embodiment, the dispenser assembly includes one or more of an actuator, a valve, a controllable aperture, an electromechanical orifice, an aperture diaphragm, an electromechanical port, an electronic oscillator for controlling a nebulizer, an ultrasonic vibrating mesh, and an electromechanical spray valve.

In an embodiment, the dispenser assembly includes one or more of a jet nebulizer, a mesh nebulizer, an ultrasonic nebulizer.

In an embodiment, at least one sensor includes a UV sensor or UV camera or a proximity sensor.

In an embodiment, the sprayer comprises a proximity sensor configured to detect a surface, and the sprayer is configured to turn on spraying upon the sensor detecting a surface.

In an embodiment, the sprayer comprises a proximity sensor configured to detect a surface, and the sprayer is configured to turn off spraying upon the sensor failing to detect a surface.

In an embodiment, the sprayer comprises a proximity sensor configured to detect a surface, and the sprayer is configured to direct the spray in the direction of the surface.

In an embodiment, the sprayer comprises a proximity sensor configured to detect a surface and the distance to the surface, and the dispenser assembly is configured to turn on spraying upon detecting a surface and the distance to the surface is within a value.

In an embodiment, the sprayer comprises a proximity sensor configured to detect a surface and the distance to the surface, and the dispenser assembly is configured to modify a spray velocity or a spray shape, or both spray velocity and spray shape, based on the distance to the surface.

In an embodiment, the sprayer comprises a UV camera, and the sprayer is configured to turn on spraying based on detecting insufficient UV sunscreen protection on a surface.

In an embodiment, the sprayer comprises a reservoir containing the formulation, wherein the reservoir supplies the dispenser assembly with the formulation.

In another aspect, a sprayer for adjusting a spray characteristic based on a sensor includes one or more electronic sensors; and a dispenser assembly being configured to adjust a spray characteristic based on an input from a sensor. In an embodiment, the spray characteristic includes one or more of a spray flow rate, a spray angle, a spray distance, a spray drop density, a spray drop size, a spray drop uniformity, a spray pattern, a spray pattern shape, a spray spaced-apart pattern, a spray stream direction, a spray velocity, and a spray volume.

In an embodiment, the dispenser assembly includes a vibrating mesh dispenser assembly, wherein the vibrating mesh dispenser assembly is configured to adjust a vibration frequency.

In an embodiment, the dispenser assembly includes a vibrating mesh dispenser assembly, wherein the vibrating mesh dispenser assembly is configured to sweep through a vibration frequency range.

In an embodiment, the dispenser assembly includes a vibrating mesh dispenser assembly, wherein the vibrating mesh dispenser assembly is configured to adjust a vibration amplitude.

In an embodiment, the dispenser assembly includes a vibrating mesh dispenser assembly, wherein the vibrating mesh dispenser assembly is configured to adjust a voltage amplitude to increase a velocity of the spray.

In an embodiment, the dispenser assembly includes a vibrating mesh dispenser assembly, wherein the vibrating mesh dispenser assembly is configured to adjust a duty cycle to increase the velocity of the spray.

In an embodiment, the dispenser assembly includes a circular vibrating mesh dispenser assembly, wherein the vibrating mesh dispenser assembly is configured to vibrate in one or more vibration drum modes.

In an embodiment, the dispenser assembly is adjustable by rotating around first and second axes.

In an embodiment, the sprayer includes a plurality of dispenser assemblies, each dispenser assembly being independently turned on.

In an embodiment, the sprayer includes a vibrating mesh dispenser assembly having a first and second mesh driven by one piezoelectric material.

In an embodiment, the sprayer includes a jet dispenser assembly, wherein the jet dispenser assembly is configured to adjust the diameter of a spray.

In an embodiment, the sprayer includes a jet dispenser assembly, wherein an orifice size is adjusted to increase or decrease flow.

In an embodiment, the dispenser assembly is a vibrating mesh, an ultrasonic wave or a jet dispenser assembly.

In another aspect, a method for spraying a formulation includes sensing a surface within spraying range of a spray dispenser assembly of the formulation.

In an embodiment, the method further comprises turning on the dispenser assembly to spray the formulation based on sensing the surface.

In an embodiment, the method further comprises adjusting a spray characteristic based on sensing the surface.

In another aspect, a method for spraying a formulation includes sensing a characteristic of a surface with a dispenser assembly of a formulation.

In an embodiment, the method further includes adjusting the dispenser assembly based on the surface characteristic.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Described are systems and methods of spraying used for delivery of formulations onto the skin or for inhalation. Spraying is a process of changing a liquid formulation into a mist of fine droplets for application topically. There are various types of electrically driven sprayers, including vibrating mesh, jet, and ultrasonic wave sprayers. This disclosure is related to all types of sprayers and is not limited to any particular spray technology.

Conventional sprayers are "dumb" in the sense that the only control is a manual on or off switch to turn on the sprayer to generate the mist and turn off the sprayer to stop the mist. In this disclosure, "smart" sprayers with one or more sensors are disclosed that increase the effectiveness of sprayers. In an embodiment, by incorporating one or more sensors, a sprayer is controllable to change the characteristics of the sprayer to more effectively spray over an area, to change the character of a spray pattern, to avoid wasting the formulation by detecting suitable areas to be sprayed, or to enable the spraying of one or more different formulations. These are just a few of the benefits that are possible through the incorporation of sensors into sprayers of formulations.

FIG. 1 is a schematic illustration of an embodiment of a sprayer 102. In an embodiment, the sprayer 102 includes a reservoir 104 to contain the formulation to be dispensed. In an embodiment, the formulation includes lotions, such as UV protective sunscreen lotion, skin moisturizers, skin medicaments, and other skin or topical treatments. In an embodiment, the sprayers are used for inhaling medicaments. In an embodiment, the sprayer 102 includes a dispenser assembly 106. In an embodiment, the dispenser assembly 106 is any type of vibrating mesh dispenser assembly, jet dispenser assembly, ultrasonic wave dispenser assembly, and the like. In an embodiment, a dispenser assembly 106 includes one or more components that are manipulated. In an embodiment, the components are manipulated electronically via through direct current battery power or through alternating current. In an embodiment, the dispenser assembly 106 including one or more components is configured to modify at least one spray characteristic of a formulation based on an input coming from one or more sensors. In an embodiment, one or more inputs from sensors are indicative of the presence or character of the surface to be sprayed.

In an embodiment, the sprayer 102 includes a jet dispenser assembly. In an embodiment, a jet dispenser assembly uses a high velocity gas to convert the formulation into an aerosol. In an embodiment, a jet dispenser assembly delivers compressed gas through a jet, which causes negative pressure. The formulation is entrained into the gas stream and is sheared into a fluid film, which breaks into fine droplets. Factors affecting the spray pattern include jet design, gas pressure, and gas density. In an embodiment, the flow or pressure of the gas is adjusted to change the characteristics of the spray produced by the jet dispenser. In an embodiment, the spray pattern diameter is adjusted through nozzle adjustment. In an embodiment, the spray volume is adjusted by changes in the orifice size.

In an embodiment, a sprayer 102 includes an ultrasonic wave dispenser assembly. In an embodiment, an ultrasonic wave dispenser assembly has a transducer with a ring-shaped piezoelectric element attached to a metal plate. The metal plate is in contact with a liquid reservoir. Generally, the metal plate is at the bottom of the formulation. As the metal plate is caused to vibrate at a high frequency, the vibrations are sufficient to produce a mist. In an embodiment, the amplitude or the frequency or both amplitude and frequency of an ultrasonic wave sprayer is adjusted to change the characteristics of the spray produced by the dispenser. In an embodiment, amplitude, duty cycle, or voltage is adjusted to change the characteristics of the spray. A spray produced by a dispenser assembly defines the plume of aerosolized fluid.

In an embodiment, a sprayer 102 includes a vibrating mesh dispenser assembly. In an embodiment, a vibrating mesh dispenser assembly includes a metallic mesh with apertures that is surrounded by a piezoelectric material. The piezoelectric material contracts and expands upon the application of an electric current. Consequently, the piezoelectric material vibrates at a high rate of speed. In an embodiment, the apertures have a tapered shape with a larger cross-section on the formulation side and a smaller cross-section on the side the droplets emerge. In an embodiment, the formulation is placed in the reservoir in contact with the mesh. Pressure builds in the vicinity of the mesh, creating a pumping action that extrudes the formulation through the apertures. Circuitry produces an analog signal of specific voltage, frequency, duty cycle, and waveform to drive the piezoelectric material. In an embodiment, anyone of these parameters is adjusted to change the character of the spray. In an embodiment, the amplitude or the frequency or both amplitude and frequency of a vibrating mesh sprayer is adjusted to change the characteristics of the spray produced by the dispenser. In an embodiment, amplitude, duty cycle, or voltage is adjusted to change the characteristics of the spray. In an embodiment, a vibrating mesh sprayer includes more than one metal mesh. In an embodiment, a vibrating mesh sprayer includes more than one piezoelectric element. In an embodiment, a vibrating mesh sprayer has a transducer horn that induces passive vibrations in the mesh. The transducer horn is in contact with the formulation. Then transducer horn vibrations cause up and down movement of a mesh plate, and the formulation passes through the apertures in the plate and forms an aerosol.

The mention of specific types of dispensers and dispenser assemblies does not limit this disclosure. This disclosure is applicable to any type of sprayer technology including, but, not limited to the jet, ultrasonic wave, and vibrating mesh sprayers.

Figure 1:
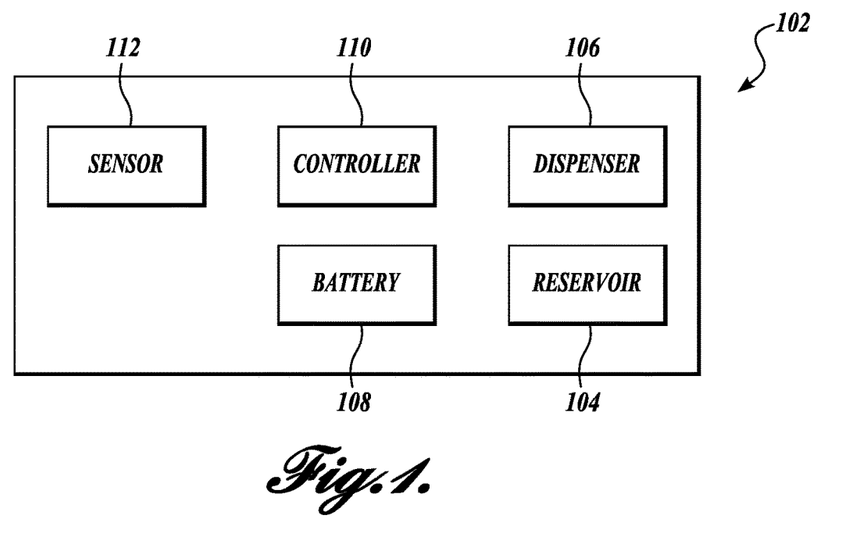
FIG. 1 is a schematic illustration of a system for dispensing a formulation.

In an embodiment, the sprayer 102 includes a battery 108 and a controller 110. In an embodiment, the controller 110 is a central processing unit (CPU) or any other type of logic controller that is programmed via software or includes circuitry hardware or both software and hardware to perform tasks as described herein. In an embodiment, the controller 102 includes signal processing and imaging processing circuitry. In an embodiment, the sprayer 102 includes a least one sensor 112. Sensors, in general, provide inputs to the controller 102. In an embodiment, the inputs include a voltage or amperage signal that represents a value of a parameter that is being measured by the sensor. For example, a temperature sensor sends a voltage input, for example, wherein the voltage is proportional of the temperature. In an embodiment, the voltage can be inversely proportional to the parameter being measured. In an embodiment, the input is a current signal instead of a voltage signal.

In an embodiment, the sensor 112 includes a UV (ultraviolet) camera. Ultraviolet is electromagnetic radiation typically considered to have a wavelength in the range of 10 nm to 400 nm. In an embodiment, the sensor 112 includes an accelerometer. In an embodiment, the sensor 112 includes an infrared sensor. Infrared is electromagnetic radiation typically considered to have a wavelength of 700 nm to 1,000,000 nm. In an embodiment, the sensor 112 includes a motion sensor. Motion sensors use a variety of technologies, including, but not limited to, passive infrared, microwave, ultrasonic, tomographic (sensing disturbances in radio waves), and visible light video cameras. In an embodiment, the sensor 112 includes a proximity sensor. Proximity sensors use a variety of technologies including, but not limited to, capacitive, eddy-current, inductive, laser, magnetic, charge-coupled devices, photocell, sonar, ultrasonic, and the like. In an embodiment, the sensor 112 includes a visible light sensor. Visible light is typically considered to have a wavelength of 400 nm to 700 nm. In an embodiment, the sensor 112 includes a pressure sensor. Pressure sensors use a variety of technologies including, but not limited to, piezoresistive strain gauge, capacitive, electromagnetic, optical, and potentiometric. In an embodiment, the sensor 112 includes a temperature sensor. Temperature sensors use a variety of technologies including, but not limited to, thermocouple, resistance, infrared, and the like. In an embodiment, the sprayer 102 with any one of the type of dispenser includes more than one of the sensor types disclosed herein.

Based on the sensor 112, the dispenser assembly 106 is controlled to carry out a particular function. In an embodiment, one or more sensors are selected to sense the presence or character or both presence and character of a surface to be sprayed. In an embodiment, one or more sensors are used to modify or adjust the spray characteristics. In an embodiment, the spray characteristic that is modified or adjusted includes, but is not limited to, one or more of a spray flow rate, a spray angle, a spray distance, a spray drop density, a spray drop size, a spray drop uniformity, a spray pattern, a spray pattern shape, a spray spaced-apart pattern, a spray stream direction, a spray velocity, and a spray volume. In an embodiment, sensing the presence of a surface is used to decide when the sprayer 102 is turned on or off. In an embodiment, sensing the distance to a surface is used to decide the pressure or power applied to the dispenser assembly so that the spray will reach the surface. In an embodiment, sensing the direction of a surface is used to direct the spray in the proper direction. In an embodiment, sensing a character of a surface, such as capturing an image of the surface with a UV camera, is used to determine what areas need to be sprayed with UV protectant sunscreen and then spray the sunscreen on those areas.

Figure 2:
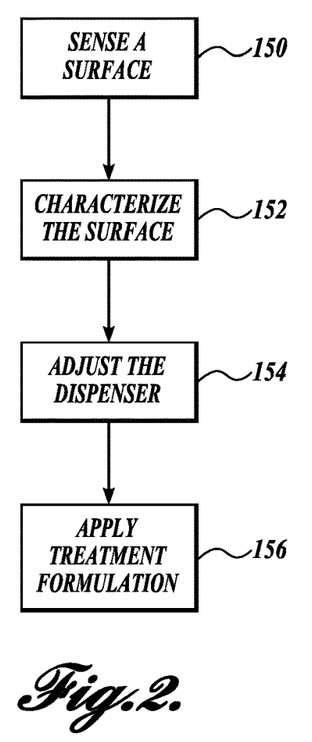
FIG. 2 is a flow diagram of a method of dispensing a formulation.

FIG. 2 is a schematic flow diagram to represent methods including steps for sensing a surface (block 150), characterizing a surface (block 152), adjusting the dispenser (block 154), and applying a formulation (block 156). In an embodiment, the method includes steps in the following order: sensing a surface (block 150), characterizing a surface (block 152), adjusting the dispenser (block 154), and applying the formulation (block 156). In an embodiment of the method, block 150 is optional. In an embodiment of the method, block 152 is optional. In an embodiment of the method, block 154 is optional. In an embodiment of the method, block 156 is optional. In an embodiment, any combination of two or more steps may be combined, for example, blocks 150 and 152, blocks 150 and 154, blocks 150 and 156, blocks 152 and 154, blocks 152 and 156, and blocks 154 and 156.

Referring to FIG. 2, in block 150, the sprayer 102 has the option of sensing a surface. In an embodiment, the surface is living tissue, for example, the skin of a person. Sensors for sensing the presence of a surface include, but are not limited to, motion sensors, infrared sensors, ultraviolet sensors, temperature sensors, light sensors, and the like. In block 102, the method includes a step for sensing the character of the surface. In an embodiment of sensing the character of a surface, an ultraviolet sensor is used to sense areas where sunscreen needs to be applied. In an embodiment, an ultraviolet camera is used to characterize the surface.

In an embodiment, blocks 154 and 156 are performed individually or together after block 150 or block 152. For example, in an embodiment, after sensing the presence of a surface, the dispenser is adjusted based on a sensor input or the formulation is applied. In an embodiment, after characterizing the surface, the dispenser assembly is adjusted or the formulation is applied.

Block 154 includes modifying or adjusting the sprayer 102 characteristics. In an embodiment, the spray characteristic include, but are not limited to, one or more of a spray flow rate, a spray angle, a spray distance, a spray drop density, a spray drop size, a spray drop uniformity, a spray pattern, a spray pattern shape, a spray spaced-apart pattern, a spray stream direction, a spray velocity, and a spray volume. Sprayer characteristics include, but are not limited to adjusting the sprayer dispenser 106 direction, adjusting the sprayer power or frequency, or adjusting the sprayer spray pattern, such as through an adjustment of the nozzle. In an embodiment, sprayer dispenser direction is adjusted for vibrating mesh sprayers, jet sprayers, and ultrasonic wave sprayers. In an embodiment, a sprayer characteristic that is adjusted includes the power applied resulting in a spray capable of traveling a greater distance. In block 156, based on input from the sensors, the controller executes instructions to decide whether or not the sprayer 102 sprays the formulation. As discussed, the decision to spray or not spray is based on detecting or not detecting a surface or a character of the surface.

In an embodiment, a sprayer 102 has a UV camera that is used to create an image of a surface. In an embodiment, the image is then analyzed via an image processor and controller 110 that measure one or more of the brightness, contrast, and intensity of UV of the surface in block 152. In an embodiment, the sprayer 102 with a UV camera optionally also includes a sensor to first sense the surface before characterizing the surface. Still further, in an embodiment, one or more of the distance, speed, direction, and acceleration of the surface are measured for characterizing the surface, and from the measurements, the dispenser 106 is adjusted.

In block 152, as part of characterizing a surface, when the sprayer 102 with a UV camera has captured an image of a surface, the electronic image taken by the UV camera is divided into a grid. In an embodiment, each square making up the grid is assigned a value. The assigned value is a measure of the UV radiation protection on scale from a minimum to a maximum. In an embodiment, for example, the value represents the intensity of UV radiation reflected from the surface. Therefore, where the reflection of UV is greatest the square is assigned a relative high value and where the reflection of UV is least a relative low value is assigned. Each square that makes up the image is so graded to arrive at a complete picture of the surface. Therefore, the sprayer has a map of areas requiring further sunscreen protection and areas that do not require sunscreen protection. Further, areas on the grid are ranked in terms of the amount of sunscreen protection required. In an embodiment, the dispenser assembly is then programmed to apply an amount of sunscreen lotion corresponding to the assigned value of UV protection. For example, in an embodiment, for areas that are ranked least in sunscreen protection, the dispenser assembly 106 is adjusted to increase the amount of sunscreen lotion delivered by increasing amplitude, pressure, voltage, and the like depending on whether the sprayer 102 is a vibrating mesh sprayer, jet sprayer, or ultrasonic wave sprayer. In an embodiment, for areas that are ranked greatest in sunscreen protection, the dispenser assembly 106 is adjusted to decrease the amount of sunscreen lotion delivered by decreasing amplitude, pressure, voltage, and the like. In areas that are deemed to have enough sunscreen protection, the sprayer simply shuts off. In other embodiments, parameters other than UV absorption or reflection can be mapped, for example, sensors that detect IR (infrared), temperature, or sound.

In another embodiment, when the sprayer has mapped a surface of areas requiring sunscreen protection, the sprayer makes adjustments according to the grade assigned to each square. In an embodiment, the sprayer adjusts dispenser assembly position to be aimed at the squares requiring sunscreen protection. In an embodiment, the sprayer adjusts dispenser assembly angle to be aimed at the grid squares requiring sunscreen protection. In an embodiment, the sprayer adjusts the power applied to the dispenser assembly. In an embodiment, the sprayer adjusts the frequency applied to the dispenser assembly. In an embodiment, the sprayer adjusts the amplitude applied to the dispenser assembly. In an embodiment, the sprayer adjusts the dispenser assembly to change the spray diameter.

As discussed, the sprayer 102 is not limited to the number of sensors for characterizing a surface. Therefore, in an embodiment, a sprayer 102 senses multiple characteristics of a surface to control the dispenser 106. In an embodiment, a sprayer 102 has a UV camera and a proximity sensor.

In an embodiment, a proximity sensor determines the distance to a surface. In an embodiment, the sprayer 102 with a proximity sensor determines whether a surface is within a distance that the spray pattern of the sprayer is designed to reach. In an embodiment, the sprayer 102 with a proximity sensor determines the area of the surface to be sprayed. In an embodiment, the sprayer 102 with a proximity sensor determines the angle of the surface with respect to the front plane of the dispenser 106. In an embodiment, the sprayer 102 with a proximity sensor determines the speed of the surface moving toward the sprayer 102. In an embodiment, the sprayer 102 determines the speed of the surface moving away from the sprayer 102. In an embodiment, the sprayer 102 determines the direction of the surface 102. In an embodiment, the sprayer determines the acceleration of the surface 102.

Referring to FIG. 2, block 154, after having sensed a surface or characterized the surface, or both sensed and characterized the surface in one or more ways, the sprayer 102 adjusts the dispenser 106 in one or more ways. In an embodiment, the spray characteristic to be manipulated or changed includes one or more of the following. Spray characteristics include, but are not limited to, one or more of a spray flow rate, a spray angle, a spray distance, a spray drop density, a spray drop size, a spray drop uniformity, a spray pattern, a spray pattern shape, a spray spaced-apart pattern, a spray stream direction, a spray velocity, and a spray volume.

Figure 3:
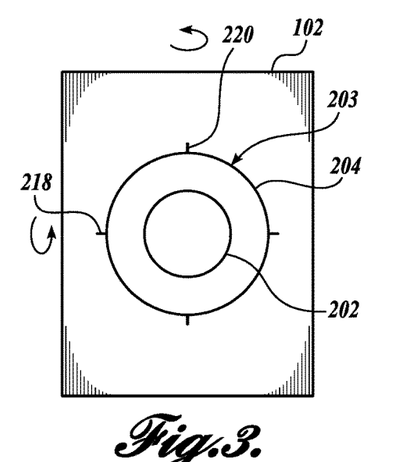
FIG. 3 is a diagrammatical illustration of a sprayer for a formulation.

In an embodiment shown in FIG. 3, a sprayer 102 is diagrammatically illustrated with a dispenser assembly 203 that rotates around two axes. In an embodiment, a vibrating mesh dispenser 203 includes a piezoelectric element 204 surrounding a metal mesh 202. In the vibrating mesh dispenser 203, the metal mesh 202 is perforated with a plurality of small apertures. The piezoelectric element 204 is concentric with the metal mesh 202. In an embodiment, the vibrating mesh dispenser 203 is gimbaled to rotate in two axes 218 and 220. Therefore, the spray pattern is directed to move up and down and from side to side. In an embodiment, a dispenser assembly on a jet sprayer or ultrasonic wave sprayer is similarly gimbaled to rotate in two axes to aim the spray at the sensed surface. In an embodiment, a sprayer 102, instead of using gimbals, uses a ball and socket for mounting the dispenser assembly 203 that allows the sprayer 102 to adjust the angle of spraying. In an embodiment, the dispenser assembly 203 is adjusted up and down and side to side when the surface to be sprayed is sensed to not be directly in front of the dispenser assembly 203. In an embodiment, for example, the dispenser assembly 203 moves up, down, left, or right to spray a surface that is sensed to lack UV protection.

Figure 4:
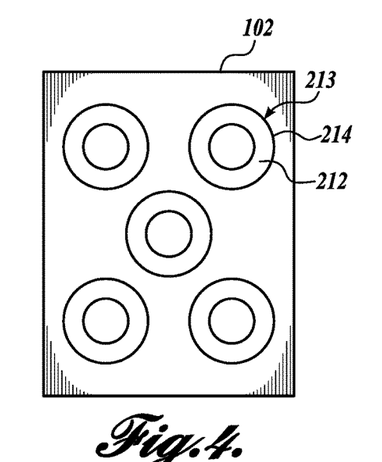
FIG. 4 is a diagrammatical illustration of a sprayer for a formulation.

In an embodiment shown in FIG. 4, a sprayer 102 is diagrammatically illustrated that has a plurality of vibrating mesh dispensers 213. An individual vibrating mesh dispenser assembly 213 includes a piezoelectric element 214 surrounding a metal mesh 212. In the vibrating mesh dispenser assembly 213, the metal mesh 212 is perforated with a plurality of small apertures. Each piezoelectric element 214 is concentric with the metal mesh 212. In an embodiment, each of the vibrating mesh dispenser assemblies 213 is turned on and off independently of all other dispenser assemblies. In an embodiment, for example, a plurality of dispenser assemblies 213 are provided on a sprayer 102, and each dispenser assembly 213 is individually connected to a different reservoir containing a different formulation. A plurality of different reservoirs may be necessary where different formulations have a different viscosity and a metal mesh with the appropriate sized apertures is required. In an embodiment, a plurality of different dispenser assemblies 213 is used which is based on the sensed characteristics of the surface. In an embodiment, the surface is sensed for more than one condition, and each different condition requires a different formulation to be used. For example, each one of a plurality of different UV sunscreen protection lotions with different SPFs (sun protection factors) is contained within a single sprayer 102. In an embodiment, the sprayer 102 rates the amount of SPF required by the surface and then applies the UV sunscreen lotion having the appropriate SPF. Further, in an embodiment, two or more sprayers are turned on or off. For example, where the surface to be covered is sensed to be rectangle shaped, two or more dispenser assemblies 213 in a row are turned on to cover the rectangular area. In an embodiment, other types of sprayers, such as a jet sprayer or an ultrasonic wave sprayer has more than one dispenser assembly.

Figure 5:
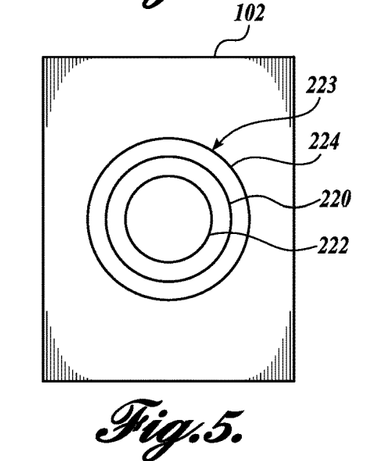
FIG. 5 is a diagrammatical illustration of a sprayer for a formulation.

In an embodiment shown in FIG. 5, a sprayer 102 having a dispenser assembly 223 with more than one metal meshes is diagrammatically illustrated. A vibrating mesh dispenser assembly 223 includes a piezoelectric element 224 surrounding a first metal mesh 220. The first metal mesh 220 surrounds a second metal mesh 222. In the vibrating mesh dispenser 223, the first metal mesh 220 is perforated with a plurality of small apertures, and the second metal mesh 222 is perforated with a plurality of small apertures. In an embodiment, the apertures of the first metal mesh 220 are different in size or shape than the apertures of the second metal mesh 222. The piezoelectric element 204, the first metal mesh 220, and the second metal mesh 222 are concentric to each other. The first metal mesh 220 is annular and the second metal mesh 222 is circular. In an embodiment, the two different meshes 220 and 222 are designed to operate at different frequencies, for example. In this way, the piezoelectric element 224 drives each metal mesh 220 or 222 independently of the other by changing the frequency or amplitude. In an embodiment, the two different meshes 220 and 222 operate simultaneously, however, the characteristics of the spray are different, for example, the flow amount through one mesh is different than the flow through the other mesh.

Figure 6:
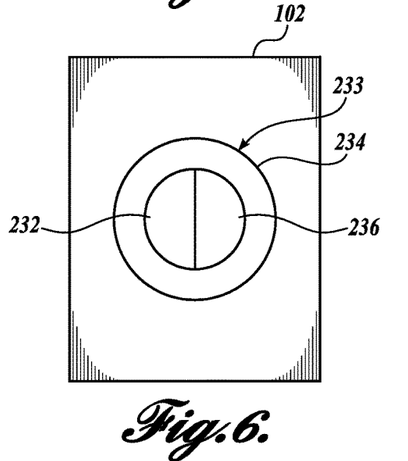
FIG. 6 is a diagrammatical illustration of a sprayer for a formulation.

In an embodiment shown in FIG. 6, a sprayer 102 with a dispenser assembly 106 having two different metal meshes incorporated side by side is diagrammatically illustrated. A vibrating mesh dispenser assembly 233 includes a piezoelectric element 234 surrounding a circular metal mesh having a first semicircular mesh half 236 and a second semicircular mesh half 232. In the vibrating mesh dispenser assembly 233, the first metal mesh half 236 is perforated with a plurality of small apertures, and the second metal mesh half 232 is perforated with a plurality of small apertures. In an embodiment, the apertures of the first metal mesh half 236 are different in size or shape than the apertures of the second metal mesh half 232. The piezoelectric element 204 is concentric with both the first metal mesh half 236 and the second metal mesh half 232. In an embodiment, the two different metal mesh halves 232 and 236 are designed to operate at different frequencies, for example. In this way, the piezoelectric element 234 drives each metal mesh half 232 or 236 independently of the other by changing the frequency or amplitude. In an embodiment, the two different mesh halves 232 and 236 operate simultaneously, however, the characteristics of the spray are different, for example, the flow amount through one mesh half is different than the flow through the other mesh half.

In an embodiment of a vibrating mesh, the metal mesh being a circular and stationary disk is caused to vibrate in one or more "drum head" modes. A drum head mode is described by the number of the nodal diameters and the nodal circles, where a node is a point or line on the metal mesh that does not move while the rest of the mesh is vibrating. Which mode is created in the metal mesh is dependent on the frequency applied to the metal mesh. In an embodiment, the driving frequency of the piezoelectric material is driven across a range of frequencies. The different mesh vibration modes apply different stresses to the fluid, which alter the fluid, such as decreasing its viscosity. The power applied to the piezo and by extension, the displacement of the mesh, may be achieved by using a pulse width modulated (PWM) output from the controller.

Figure 7:
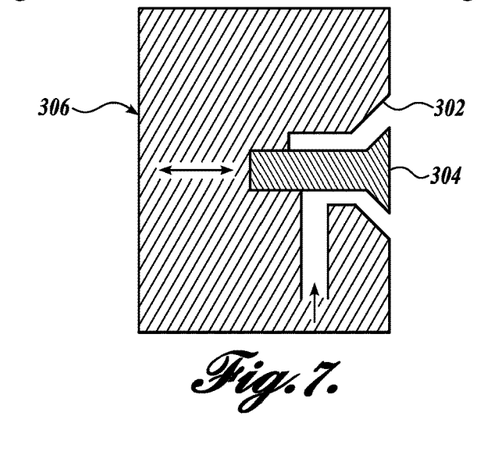
FIG. 7 is a diagrammatical illustration of a sprayer for a formulation.

In an embodiment shown in FIG. 7, a dispenser assembly 306 for a jet sprayer has a cone-shaped outlet 302 and a plug 304 positioned concentrically within the aperture. The plug 304 has frustoconical sides. The arrangement of outlet cone 302 and plug 304 creates an annular spray pattern. The plug 304 is adjustable forwards and backwards along its center axis. When the plug 304 is moved forward, the spray pattern narrows in diameter, and ultimately results in a narrow spray stream. Accordingly, in one embodiment, the coverage diameter of a spray pattern for a jet sprayer is adjustable. In an embodiment, the spray shape of a jet sprayer is adjustable by changing the position of the plug 304. In an embodiment, the spray shape of a jet sprayer is adjustable by changing the orifice size based on the position of the plug 304. In an embodiment, a jet sprayer is adjustable by increasing or decreasing the pressure of the fluid, thus, being able to propel the formulation greater distances. In an embodiment, a jet sprayer is adjustable by increasing or decreasing the pressure of the fluid, thus being able to increase or decrease spray velocity.

The various types of dispenser assemblies of this disclosure include, but are not limited to, dispenser assembly components including one or more of an actuator, a valve, a controllable aperture, an electromechanical orifice, an aperture diaphragm, an electromechanical port, an electronic oscillator for controlling a nebulizer, an ultrasonic vibrating mesh, and an electromechanical spray valve.

In view of the foregoing discussion of sprayers, in one aspect of this disclosure, a sprayer that senses the presence or character of a surface to be sprayed comprises one or more electronic sensors configured to sense the presence or character of a surface to be sprayed; and a dispenser assembly being configured to spray a formulation based on a reading coming from at least one sensor. In an embodiment, the sprayer comprises a jet dispenser assembly, a vibrating mesh dispenser assembly, or an ultrasonic wave dispenser assembly.

In another aspect, a sprayer that senses the presence or character of a surface to be sprayed includes one or more sensors configured to detect a presence or character of a surface to be sprayed; and a dispenser assembly including one or more components configured to modify at least one spray characteristic of a formulation based on an input from at least one of the one or more sensors indicative of the presence or character of the surface to be sprayed. In an embodiment, the dispenser assembly includes one or more of a jet dispenser, a vibrating mesh dispenser, and an ultrasonic wave dispenser. In an embodiment, the spray characteristic includes one or more of a spray flow rate, a spray angle, a spray distance, a spray drop density, a spray drop size, a spray drop uniformity, a spray pattern, a spray pattern shape, a spray spaced-apart pattern, a spray stream direction, a spray velocity, and a spray volume based on an input from at least one of the one or more sensors indicative of the presence or character of the surface to be sprayed. In an embodiment, the dispenser assembly includes one or more components configured to modify at least one spray characteristic of a formulation based on an input from at least one of the one or more sensors indicative of a surface area to be sprayed. In an embodiment, the dispenser assembly includes one or more of an actuator, a valve, a controllable aperture, an electromechanical orifice, an aperture diaphragm, an electromechanical port, an electronic oscillator for controlling a nebulizer, an ultrasonic vibrating mesh, and an electromechanical spray valve. In an embodiment, the dispenser assembly includes one or more of a jet nebulizer, a mesh nebulizer, an ultrasonic nebulizer. In an embodiment, the sprayer includes at least one sensor including a UV sensor or UV camera or a proximity sensor. In an embodiment, the sprayer includes a proximity sensor configured to detect a surface, and the sprayer is configured to turn on spraying upon the sensor detecting a surface. In an embodiment, the sprayer includes a proximity sensor configured to detect a surface, and the sprayer is configured to turn off spraying upon the sensor failing to detect a surface. In an embodiment, the sprayer includes a proximity sensor configured to detect a surface, and the sprayer is configured to direct the spray in the direction of the surface. In an embodiment, the sprayer includes a proximity sensor configured to detect a surface and the distance to the surface, and the dispenser assembly is configured to turn on spraying upon detecting a surface and the distance to the surface is within a value. In an embodiment, the sprayer includes a proximity sensor configured to detect a surface and the distance to the surface, and the dispenser assembly is configured to modify a spray velocity or a spray shape or both spray velocity and spray shape based on the distance to the surface. In an embodiment, the sprayer includes a UV camera, and the sprayer is configured to turn on spraying based on detecting insufficient UV sunscreen protection on a surface. In an embodiment, the sprayer includes a reservoir containing the formulation, wherein the reservoir supplies the dispenser assembly with the formulation.

In another aspect of this disclosure, a sprayer for adjusting a spray characteristic based on a sensor includes one or more electronic sensors; and a dispenser assembly being configured to adjust a spray characteristic based on an input from a sensor. In an embodiment, the spray characteristic includes one or more of a spray flow rate, a spray angle, a spray distance, a spray drop density, a spray drop size, a spray drop uniformity, a spray pattern, a spray pattern shape, a spray spaced-apart pattern, a spray stream direction, a spray velocity, and a spray volume. In an embodiment, the dispenser assembly includes a vibrating mesh dispenser assembly, wherein the vibrating mesh dispenser assembly is configured to adjust a vibration frequency. In an embodiment, the dispenser assembly includes a vibrating mesh dispenser assembly, wherein the vibrating mesh dispenser assembly is configured to sweep through a vibration frequency range. In an embodiment, the dispenser assembly includes a vibrating mesh dispenser assembly, wherein the vibrating mesh dispenser assembly is configured to adjust a vibration amplitude. In an embodiment, the dispenser assembly includes a vibrating mesh dispenser assembly, wherein the vibrating mesh dispenser assembly is configured to adjust a voltage amplitude to increase a velocity of the spray. In an embodiment, the dispenser assembly includes a vibrating mesh dispenser assembly, wherein the vibrating mesh dispenser assembly is configured to adjust a duty cycle to increase the velocity of the spray. In an embodiment, the dispenser assembly includes a circular vibrating mesh dispenser assembly, wherein the vibrating mesh dispenser assembly is configured to vibrate in one or more vibration drum modes. In an embodiment, the dispenser assembly is adjustable by rotating around first and second axes. In an embodiment, the sprayer includes a plurality of dispenser assemblies, each dispenser assembly being independently turned on. In an embodiment, the sprayer includes a vibrating mesh dispenser assembly having a first and second mesh driven by one piezoelectric material. In an embodiment, the sprayer includes a jet dispenser assembly, wherein the jet dispenser assembly is configured to adjust the diameter of a spray. In an embodiment, the sprayer includes a jet dispenser assembly, wherein an orifice size is adjusted to increase or decrease flow. In an embodiment, the dispenser assembly is a vibrating mesh, an ultrasonic wave or a jet dispenser assembly. In an embodiment, a sprayer device with a sensor array that utilizes an ultrasonic mesh nebulizer or sprayer for dispensing a fluid receives inputs of the distance and character of the surface to be sprayed and adjusts the character of the spray accordingly. In an embodiment of an ultrasonic mesh nebulizer sprayer, voltage amplitude or duty cycle is increased to increase the velocity of the particles being sprayed to reach the target surface. In an embodiment of a propellant based sprayer, the size of the orifice could be adjusted to allow greater flow to cover a larger area on the target surface, etc.

In another aspect of this disclosure, a method for spraying a formulation comprises sensing a surface within spraying range of a spray dispenser of the formulation. In an embodiment, the method includes turning on the dispenser assembly to spray the formulation based on sensing the surface. In an embodiment, the method includes adjusting a spray characteristic based on sensing the surface.

In another aspect of this disclosure, a method for spraying a formulation comprises sensing a characteristic of a surface with a dispenser assembly of a formulation. In an embodiment, the method includes adjusting the dispenser assembly based on the surface characteristic.

While illustrative embodiments have been illustrated and described, it will be appreciated that various changes can be made therein without departing from the spirit and scope of the invention.

The embodiments of the invention in which an exclusive property or privilege is claimed are defined as follows:

1. A sprayer that senses a character of a surface to be sprayed, comprising:
   one or more sensors configured to detect a character of a surface to be sprayed, wherein the surface is living tissue and wherein at least one sensor determines at least one surface character selected from a surface area to be sprayed, an angle of a surface with respect to a front plane of the sprayer, a speed of a surface moving toward the sprayer, a speed of a surface moving away from the sprayer, an acceleration of a surface moving toward or away from the sprayer; and
   a dispenser assembly including one or more components configured to modify at least one spray characteristic based on an input from at least one of the one or more sensors indicative of the character of the surface to be sprayed, wherein the dispenser assembly includes a vibrating mesh dispenser assembly, wherein the vibrating mesh dispenser assembly has a first and second mesh driven by one piezoelectric element, and further wherein the piezoelectric element is concentrically placed around an outer periphery of the first or second mesh.

2. The sprayer of claim 1, wherein the spray characteristic includes one or more of a spray flow rate, a spray angle, a spray distance, a spray drop density, a spray drop size, a spray pattern, a spray pattern shape, a spray stream direction, a spray velocity, and a spray volume based on an input from at least one of the one or more sensors indicative of the character of the surface to be sprayed.

3. The sprayer of claim 1, wherein the dispenser assembly includes one or more components configured to modify at least one spray characteristic based on an input from at least one of the one or more sensors indicative of a surface area to be sprayed.

4. The sprayer of claim 1, wherein the dispenser assembly includes one or more of an actuator, a valve, a controllable aperture, an electromechanical orifice, an aperture diaphragm, an electromechanical port, an electronic oscillator for controlling a nebulizer, an ultrasonic vibrating mesh, and an electromechanical spray valve.

5. The sprayer of claim 1, wherein the dispenser assembly includes one or more of a mesh nebulizer and an ultrasonic nebulizer.

6. The sprayer of claim 1, wherein at least one sensor includes a UV sensor or UV camera or a proximity sensor.

7. The sprayer of claim 1, comprising a proximity sensor configured to detect a surface, and the sprayer is configured to turn on spraying upon the sensor detecting a surface.

8. The sprayer of claim 1, comprising a proximity sensor configured to detect a surface, and the sprayer is configured to turn off spraying upon the sensor failing to detect a surface.

9. The sprayer of claim 1, comprising a proximity sensor configured to detect a surface, and the sprayer is configured to direct the spray in the direction of the surface.

10. The sprayer of claim 1, comprising a proximity sensor configured to detect a surface and the distance to the surface, and the dispenser assembly is configured to turn on spraying upon detecting a surface and the distance to the surface is within a value.

11. The sprayer of claim 1, comprising a proximity sensor configured to detect a surface and the distance to the surface, and the dispenser assembly is configured to modify a spray velocity or a spray shape or both spray velocity and spray shape based on the distance to the surface.

12. The sprayer of claim 1, further comprising a UV camera, and the sprayer is configured to turn on spraying based on detecting insufficient UV sunscreen protection on a surface.

13. The sprayer of claim 1, comprising a reservoir containing the formulation, wherein the reservoir supplies the dispenser assembly with the formulation.

14. A sprayer for adjusting a spray characteristic based on a sensor, comprising:
one or more electronic sensors; and
a dispenser assembly configured to generate a spray, wherein the dispenser assembly comprises a controller being configured to adjust more than one spray characteristic based on an input received from a sensor, wherein the dispenser assembly includes a vibrating mesh dispenser assembly, wherein the vibrating mesh dispenser assembly has a first and second mesh driven by one piezoelectric element, and further wherein the piezoelectric element is concentrically placed around an outer periphery of the first or second mesh, wherein adjustable spray characteristics
include one or more spray characteristics selected from a spray flow rate, a spray angle, a spray distance, a spray stream direction, a spray velocity, a spray volume, a spray drop size, a spray pattern, and a spray pattern shape, and
at least one spray characteristic of spray drop density.

15. The sprayer of claim 14, wherein the vibrating mesh dispenser assembly is configured to adjust a vibration frequency.

16. The sprayer of claim 14, wherein the vibrating mesh dispenser assembly is configured to sweep through a vibration frequency range.

17. The sprayer of claim 14, wherein the vibrating mesh dispenser assembly is configured to adjust a vibration amplitude.

18. The sprayer of claim 14, wherein the dispenser assembly includes a vibrating circular mesh driven by a piezoelectric element, wherein the vibrating circular mesh is configured to vibrate in one or more vibration drum modes, and a controller being configured to adjust a spray characteristic by driving the piezoelectric element at a frequency to produce in the vibrating circular mesh a number of nodal diameters or nodal circles where the mesh does not move while the rest of the mesh is vibrating.

19. The sprayer of claim 14, wherein the dispenser assembly is adjustable by rotating around first and second axes.

20. The sprayer of claim 14, wherein the sprayer includes a plurality of dispenser assemblies, each dispenser assembly being independently turned on.

21. A method for spraying a formulation, comprising:
sensing a characteristic of a surface with a dispenser assembly of a formulation, wherein the surface characteristic is selected from a surface area to be sprayed, an angle of a surface with respect to a front plane of the sprayer, a speed of a surface moving toward the sprayer, a speed of a surface moving away from the sprayer, an acceleration of a surface moving toward or away from the sprayer; and
adjusting a frequency or amplitude of a vibrating mesh dispenser assembly to spray the formulation, wherein the vibrating mesh dispenser assembly has a first and second mesh driven by one piezoelectric element, and further wherein the piezoelectric element is concentrically placed around an outer periphery of the first or second mesh.

22. The method of claim 21, further comprising adjusting the dispenser assembly based on the surface characteristic.

* * * * *